United States Patent
Lee et al.

(10) Patent No.: US 11,045,642 B2
(45) Date of Patent: Jun. 29, 2021

(54) TRANSCRANIAL DIRECT CURRENT STIMULATION APPARATUS

(71) Applicant: Y-BRAIN INC, Daejeon (KR)

(72) Inventors: Ki-won Lee, Daejeon (KR); Cheon-Ju Ko, Yongin-si (KR); Jong-Min Jang, Hwaseong-si (KR); Byung-Gik Kim, Daegu (KR)

(73) Assignee: Y-BRAIN INC, Daejeon (KR)

( * ) Notice: Subject to any disclaimer, the term of this patent is extended or adjusted under 35 U.S.C. 154(b) by 196 days.

(21) Appl. No.: 15/770,459

(22) PCT Filed: Oct. 20, 2016

(86) PCT No.: PCT/KR2016/011848
§ 371 (c)(1),
(2) Date: Apr. 23, 2018

(87) PCT Pub. No.: WO2017/069541
PCT Pub. Date: Apr. 27, 2017

(65) Prior Publication Data
US 2018/0311496 A1    Nov. 1, 2018

(30) Foreign Application Priority Data

Oct. 22, 2015   (KR) .......................... 10-2015-0147464

(51) Int. Cl.
*A61N 1/04*         (2006.01)
*A61N 1/36*         (2006.01)
*A61N 1/20*         (2006.01)

(52) U.S. Cl.
CPC ............. *A61N 1/04* (2013.01); *A61N 1/0404* (2013.01); *A61N 1/0456* (2013.01);
(Continued)

(58) Field of Classification Search
CPC ...... A61N 1/08; A61N 1/0496; A61N 1/0456; A61N 1/04; A61N 1/0404; A61N 1/20
See application file for complete search history.

(56) References Cited

U.S. PATENT DOCUMENTS 8,903,494 B2 * 12/2014 Goldwasser ....... A61N 1/36025
607/45
2009/0132010 A1 * 5/2009 Kronberg ................. A61N 1/32
607/72

(Continued)

FOREIGN PATENT DOCUMENTS

KR        100915320 B1    9/2009
KR        1020110086611 A  7/2011
(Continued)

OTHER PUBLICATIONS

International Search Report dated Jan. 31, 2017, corresponding to International Application No. PCT/KR2016/011848 citing the above reference(s).

*Primary Examiner* — Rex R Holmes
(74) *Attorney, Agent, or Firm* — Hauptman Ham, LLP (57) ABSTRACT

A transcranial direct current stimulation (tDCS) apparatus includes a stimulation unit, a control unit, and an input/output (I/O) unit. The stimulation unit includes a power-supply unit to supply power for electrical stimulation corresponding to a control signal received from the control unit, and a plurality of stimulation electrodes, each of which has a hydrogel patch, to provide electrical stimulation to a living body upon receiving the power from the power-supply unit. The control unit is configured to control an on/off function of the power-supply unit such that the power-supply unit is turned on or off according to the amount of power applied to the stimulation electrodes and a time period during which the power is supplied or not supplied.

8 Claims, 6 Drawing Sheets

(52) U.S. Cl.
CPC ......... *A61N 1/0496* (2013.01); *A61N 1/3603* (2017.08); *A61N 1/20* (2013.01)

(56) References Cited

U.S. PATENT DOCUMENTS

| | | | |
|---|---|---|---|
| 2011/0190569 A1* | 8/2011 | Simon | A61N 1/18 600/26 |
| 2013/0204315 A1* | 8/2013 | Wongsarnpigoon | A61N 1/36021 607/45 |
| 2015/0088227 A1 | 3/2015 | Shishilla et al. | |

FOREIGN PATENT DOCUMENTS

| | | | |
|---|---|---|---|
| KR | 101465593 B1 | | 11/2014 |
| KR | 101473433 B1 | | 12/2014 |
| KR | 101539658 B1 | * | 7/2015 |
| KR | 101539658 B1 | | 7/2015 |
| KR | 101542780 B1 | | 8/2015 |

\* cited by examiner

TRANSCRANIAL DIRECT CURRENT STIMULATION APPARATUS

CROSS REFERENCE TO RELATED APPLICATION

This present application is a national stage filing under 35 U.S.C § 371 of PCT application number PCT/KR2016/011848 filed on Oct. 20, 2016 which is based upon and claims the benefit of priority to Korean Patent Application No. 10-2015-0147464 filed on Oct. 22, 2015, in the Korean Intellectual Property Office. The disclosures of the above-listed applications are hereby incorporated by reference herein in their entirety.

TECHNICAL FIELD

The present disclosure relates to a transcranial direct current stimulation (tDCS) apparatus.

BACKGROUND ART

A brain acting as an internal organ of a human head is the most important central nervous organ of the nervous system, and is classified into the cerebrum, the cerebellum, the midbrain, the pons, and the medulla oblongata (myelencephalon). The brain generates brainwaves obtained when the sum of neuronal activity levels is measured in the epidermis of the brain.

There are various methods for measuring the state of the brain, for example, an electroencephalogram (EEG) test for measuring/testing brainwaves received from an electrode included in a pad attached to a scalp, a computed tomography (CT) test of CT-scanning the brain using radiation or ultrasound at various angles, and a magnetic resonance imaging (MRI) test of MR-imaging the brain.

In addition, brain stimulation technology for accomplishing a given purpose by stimulating the brain is largely classified into an invasive brain stimulation method and a non-invasive brain stimulation method.

The invasive brain stimulation technology is a method of inserting an electrode into the brain through a surgery and applying electrical signals to the electrode. The non-invasive brain stimulation technology is a method of stimulating the brain without inserting the electrode into the brain so as to accomplish given effects.

In more detail, the brain stimulation technology may include a deep electrical stimulation method, a transcranial magnetic stimulation (TMS) method, a transcranial electrical stimulation (TES) method, a transcranial direct current stimulation (tDCS) method, a transcranial random noise stimulation (tRNS) method, etc.

From among the above-mentioned brain stimulation methods, the transcranial direct current stimulation (tDCS) method is a relatively simple non-invasive brain stimulation method. The transcranial direct current stimulation (tDCS) method is well known to be effective not only in improving cognitive ability, but also in treating mental illnesses such as depression or ADHD (Attention Deficit Hyperactivity Disorder). Therefore, many developers and companies are conducting intensive research into transcranial direct current stimulation (tDCS) associated technologies.

Generally, each of the EEG measurement apparatus and the brain stimulation apparatus such as tDCS includes a plurality of electrodes. That is, each of the EEG measurement apparatus and the brain stimulation apparatus such as tDCS is designed to use a single electrode as a measurement or stimulation unit, such that the EEG measurement apparatus may measure EEG signals at various positions of a human head or the brain stimulation apparatus may apply electrical stimulation to various positions of the human head.

Electrodes included in the EEG measurement apparatus and the brain stimulation apparatus, etc. may be classified into a wet electrode and a dry electrode.

The wet electrode is configured to use a chemical reaction generated to move charges at an interface between an electrolyte having no free electrons and an electrode having no ions. The wet electrode may be fixed to the skin well using a conductive adhesive or gel (hereinafter referred to as an electrolyte), and may reduce impedance of the skin to enable the signal to be well measured.

The dry electrode has been studied to overcome inconvenience of the wet electrode, such as use of an electrolyte. A conventional dry electrode may include a patch including a hydrogel layer having high impedance. A detailed configuration of the dry electrode or a configuration of the patch have been disclosed in the related art associated with a biological electrode field, including Korean Patent Registration Nos. 10-1539658 (entitled "DRY ELECTRODE") and 10-1473433 (entitled "PATCH APPARATUS") filed by the same applicant as the present disclosure.

A hydrogel patch provided on the dry electrode of the transcranial direct current stimulation (tDCS) apparatus is typically configured for single use only. In more detail, if direct current (DC) stimulation is applied to a living body through the hydrogel patch attached to the living body, energy corresponding to a current applied to the living body may hydrolyze water ($H_2O$) included in the hydrogel, and polarization may occur in an electromagnetic field formed by the current, resulting in polarization of acidic/basic ions. As a result, the hydrogel patch used once may cause pH imbalance between each electrode and the skin, resulting in damage to skin tissues. Therefore, the hydrogel patch used once is generally discarded.

The above-mentioned disposable hydrogel patch has a disadvantage in that it unavoidably increases operating costs of the transcranial direct current stimulation (tDCS) apparatus and causes the environmental pollution.

Disclosure

Technical Problem

An object of the present disclosure is to provide a transcranial direct current stimulation (tDCS) apparatus configured in a manner that a hydrogel patch provided on an electrode for attachment to a living body can be reused.

Objects of the present disclosure are not limited to the above-described objects and other objects and advantages can be appreciated by those skilled in the art from the following descriptions. Further, it will be easily appreciated that the objects and advantages of the present disclosure can be practiced by means recited in the appended claims and a combination thereof.

Technical Solution

The object of the present disclosure can be achieved by providing a transcranial direct current stimulation apparatus including a stimulation unit, a control unit, and an input/output (I/O) unit. The stimulation unit includes a power-supply unit to supply power for electrical stimulation corresponding to a control signal received from the control unit, and a plurality of stimulation electrodes, each of which has a hydrogel patch, to provide electrical stimulation to a living body upon receiving the power from the power-supply unit. The control unit is configured to control an on/off function of the power-supply unit such that the power-supply unit is turned on or off according to the amount of power applied to the stimulation electrodes and a time period during which the power is supplied or not supplied.

The control unit may control the ON function of the power-supply unit during a prescribed time in a manner that the power-supply unit is turned on according to the amount of power applied to each of the stimulation electrodes or a continuous power supply time for each stimulation electrode.

The control unit may turn off the power-supply unit when the amount of power applied to each of the stimulation electrodes or a power supply time for each stimulation electrode is greater than a reference value. The control unit may calculate and establish, in real time, a reference power-supply value capable of being applied to each stimulation electrode in a manner that the reference power-supply value corresponds to a time period during which power is not supplied to each of the stimulation electrodes.

The prescribed time may be established by real-time calculation of the control unit in a manner that the prescribed time corresponds to the amount of power applied to each of the stimulation electrodes or a power supply time for each stimulation electrode.

Advantageous Effects

As is apparent from the above description, the transcranial direct current stimulation (tDCS) apparatus according to an embodiment of the present disclosure is configured in a manner that a hydrogel patch provided on an electrode for attachment to a living body can be reused.

Therefore, the embodiment of the present disclosure may reduce the operating costs of the transcranial direct current stimulation (tDCS) apparatus, and may prevent the environment pollution caused by the use of disposable hydrogel patches.

BEST MODE

The above objects, features and advantages will become apparent from the detailed description with reference to the accompanying drawings.

The specific structural and functional description of the exemplary embodiments of the present disclosure, which are disclosed in the specification of the invention, is merely an exemplary description provided for the purpose of describing the exemplary embodiments according to the present disclosure. The present disclosure may be embodied in many different forms and should not be construed as being limited to the embodiments set forth herein.

Since diverse variations and modifications may be applied to the exemplary embodiments according to the concept of the present disclosure, and since the exemplary embodiments of the present disclosure may be configured in diverse forms, a specific embodiment of the present disclosure will hereinafter be described in detail with reference to the examples presented in the accompanying drawings. However, it should be understood that the exemplary embodiments respective to the concept of the present disclosure are not limited only to the specific structures disclosed herein. Therefore, it should be understood that all variations and modifications, equivalents, and replacements, which are included in the technical scope and spirit of the present disclosure, are included.

It will be understood that the terms "first" and "second" are used herein to describe various elements and are only used to distinguish one element from another element. Thus, a first element may be termed a second element, and similarly, a second element may be termed a first element without departing from the teachings of the present disclosure.

It will be understood that when an element is referred to as being "connected to" another element, it can be directly connected to the other element, or intervening elements may also be present. In contrast, when an element is referred to as being "directly connected to" another element, no intervening elements are present. Other expressions describing relationships between components, such as "between", "directly between", "adjacent to" and "directly adjacent to", may be construed similarly.

Terms used in the following description are used only to describe the specific embodiments and are not intended to restrict the present disclosure. The expression of singularity includes a plural meaning unless the singular expression is explicitly distinguishing based on the context. In the specification, the terms "comprising," "including," and "having" shall be understood to designate the presence of particular features, numbers, steps, operations, elements, parts, or combinations thereof, but not to preclude the presence or addition of one or more other features, numbers, steps, operations, elements, parts, or combinations thereof.

Unless otherwise defined, all terms used herein, which include technical or scientific terms, have the same meanings as those generally appreciated by those skilled in the art. The terms, such as ones defined in common dictionaries, should be interpreted as having the same meanings as terms in the context of the pertinent technology, and should not be interpreted as having ideal or excessively formal meanings unless clearly defined in the specification.

Figure 1:
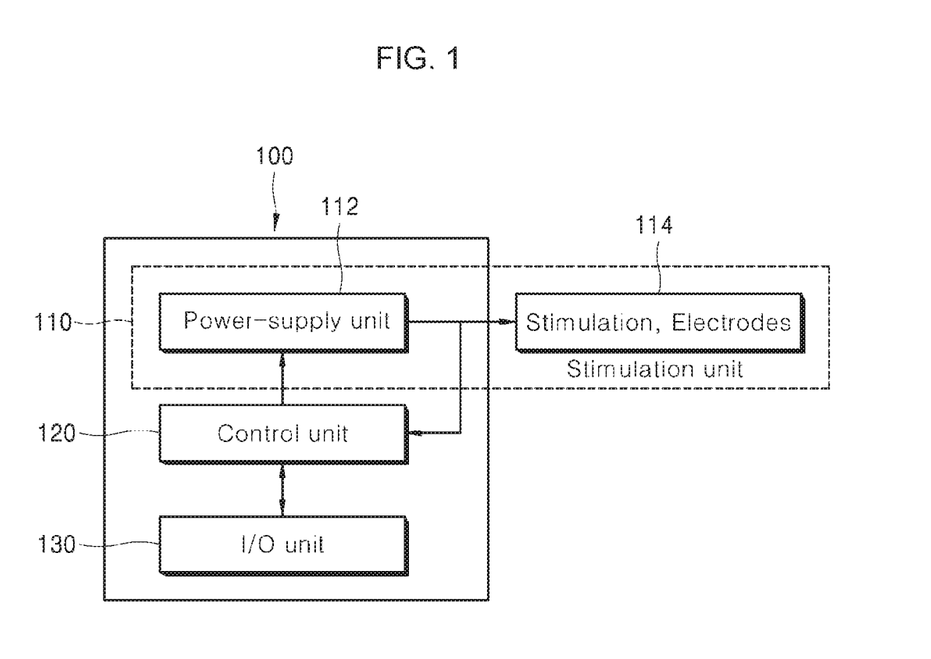
FIG. 1 is a block diagram illustrating a transcranial direct current stimulation (tDCS) apparatus according to an embodiment of the present disclosure.

FIG. 1 is a block diagram illustrating a transcranial direct current stimulation (tDCS) apparatus 100 according to an embodiment of the present disclosure.

Referring to FIG. 1, the transcranial direct current stimulation (tDCS) apparatus 100 may include a stimulation unit 110, a control unit 120, and an input/output (I/O) unit 130.

The stimulation unit 110 may include a power-supply unit 112 and a plurality of stimulation electrodes 114.

The power-supply unit 112 may supply power to the stimulation electrodes 114 according to a control signal of the control unit 120. Each of the stimulation electrodes 114 may apply a stimulation signal to the scalp upon receiving power from the power-supply unit 110.

The control unit 120 may generate a control signal upon receiving a user manipulation command or the like from the input/output (I/O) unit 130.

Based on the control signal of the control unit 120, the power-supply unit 112 of the stimulation unit 110 may generate an electric signal to be applied to the human body through the stimulation electrodes 114.

The input/output (I/O) unit 130 may receive a manipulation command from the user, and may display information regarding a current operation state of the apparatus. For example, the input/output (I/O) unit 130 may be implemented not only as a general input device such as a keyboard or mouse, but also as a display device such as a monitor.

Although not shown in FIG. 1, the transcranial direct current stimulation (tDCS) apparatus 100 according to the embodiment of the present disclosure may further include a measurement unit to measure brainwaves of the user, and the like. In this case, it will be apparent to those skilled in the art that the control unit 120 is configured to generate a control signal using signals received from the measurement unit.

As illustrated in FIG. 1, the control unit 120 of the transcranial direct current stimulation (tDCS) apparatus 100 according to the embodiment of the present disclosure may receive, in real time, information regarding the amount of power applied from the power-supply unit 112 to the stimulation electrodes 114 or information regarding the power supply time from the power-supply unit 112. The control unit 120 may control the power-supply unit 112 based on the information received from the control unit 120.

The control unit 120 of the transcranial direct current stimulation (tDCS) apparatus 100 according to the embodiment of the present disclosure will hereinafter be described with reference to FIGS. 2 to 6.

Figure 2:
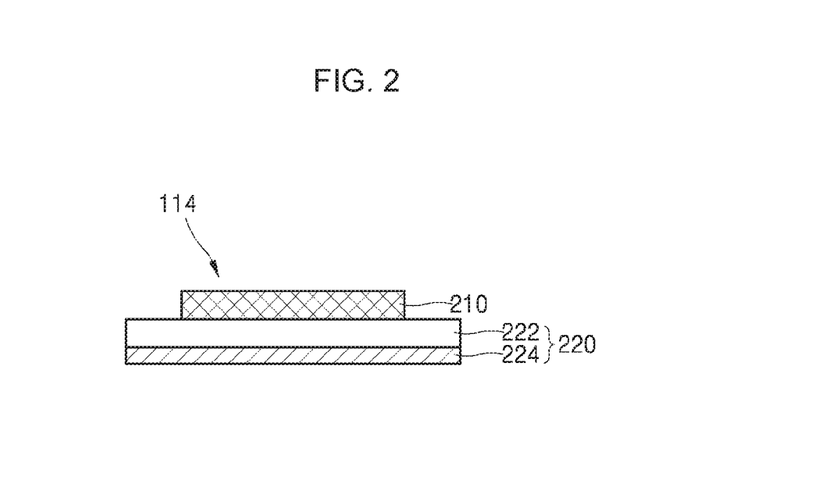
FIG. 2 is a view illustrating a stimulation electrode illustrated in FIG. 1.

FIG. 2 is a view illustrating the stimulation electrode illustrated in FIG. 1. FIGS. 3 to 6 are views illustrating the results of neutralization experiments on a hydrogel patch of the stimulation electrode illustrated in FIG. 2.

Referring to FIG. 2, the stimulation electrodes 114 (see FIG. 1) included in the transcranial direct current stimulation (tDCS) apparatus may include a conductive body 210 and a hydrogel patch 220. The hydrogel patch 220 may be formed of a stacked structure of a first hydrogel layer 222 and a second hydrogel layer 224.

When direct current (DC) power is applied to the hydrogel patch 220, hydrolysis of water ($H_2O$) included in the hydrogel patch and pH imbalance caused by hydrolysis-based polarization may occur, such that skin tissues of the user may be damaged. Therefore, it is preferable that the hydrogel patch be discarded after being used once.

However, it has been experimentally confirmed that usability of the polarized hydrogel patch 220 is recovered according to lapse of time, and the present disclosure has been proposed to maximally utilize the above-mentioned characteristics of the hydrogel patch 220.

In other words, referring to FIGS. 3 to 6, it is confirmed that the usability of the hydrogel patch 220 used one or more times for electric stimulation for 30 minutes using a power source having DC 2 mA is recovered to a substantially original state of the hydrogel patch 220, after lapse of a predetermined threshold period (e.g., 8 hours). In addition, it can also be confirmed that the usability recovery characteristics of the hydrogel patch 220 indicate that the hydrogel patch 220 can be reused several times.

Figure 4:
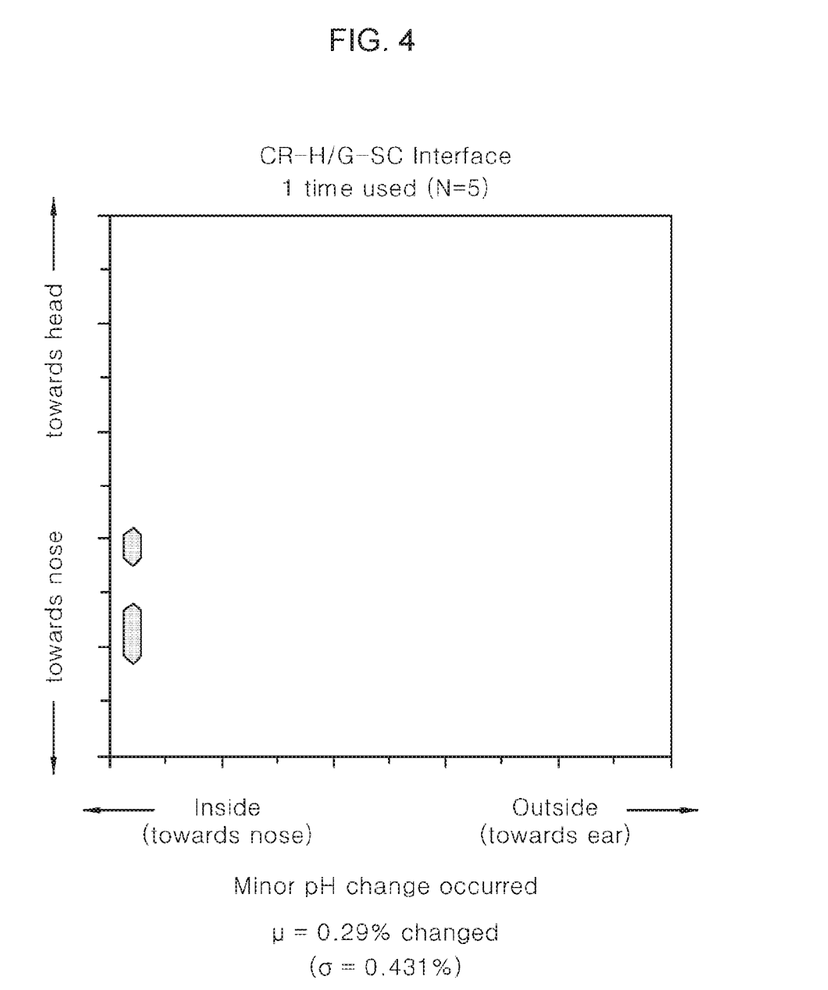
Figure 5:
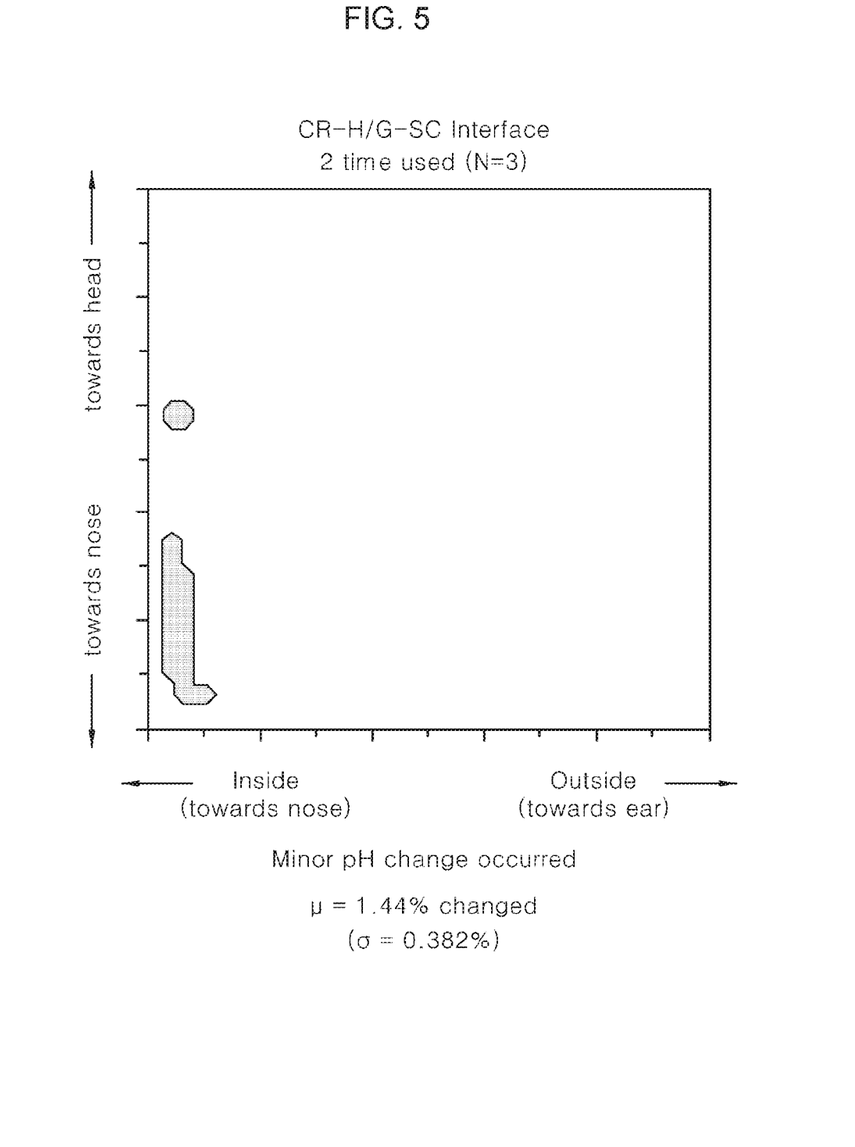
Figure 6:
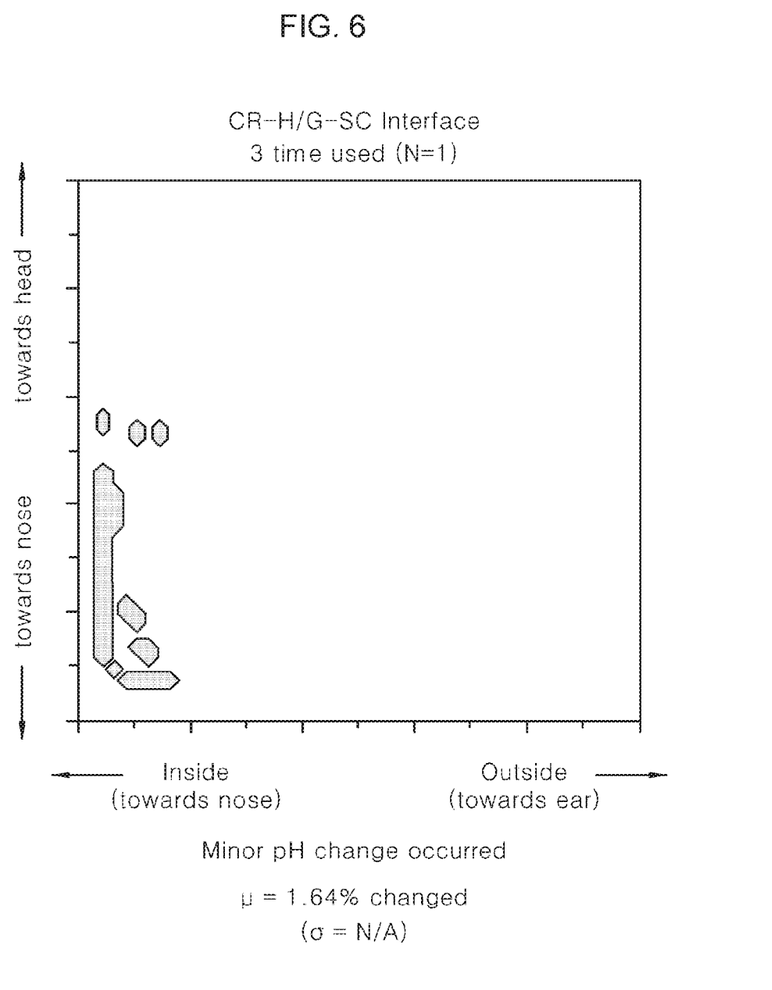

FIGS. 4 to 6 illustrate pH states at an interface between the first hydrogel layer 222 (see FIG. 2) and the second hydrogel layer 224 (see FIG. 2) in a double-structured hydrogel patch 220 (see FIG. 2).

FIG. 4 illustrates the hydrogel patch 220 used once. In more detail, FIG. 4 illustrates a pH state at the interface of the hydrogel patch 220 after lapse of 8 hours from a time point of electrical stimulation that is applied to a human body for 30 minutes using DC 2 mA power. In this case, a pH change rate is about 0.29%, and the ratio of a pH change region to the entire region is about 0.431%.

FIG. 5 illustrates an exemplary case in which the hydrogel patch 220 is used twice. In more detail, FIG. 5 illustrates a pH state after execution of re-stimulation (e.g., two stimulations) at a specific time at which the usability of the hydrogel patch 220 is recovered after lapse of 8 hours from execution of the stimulation of FIG. 4. In this case, the pH change rate is about 1.44%, and the ratio of the pH change region to the entire region is about 0.382%.

FIG. 6 illustrates an exemplary case in which the hydrogel patch 220 is used three times. In more detail, FIG. 6 illustrates a pH state of the interface of the hydrogel patch re-stimulated after lapse of 8 hours from execution of the stimulation of FIG. 5. In this case, the pH change rate is about 1.64%.

Figure 3:
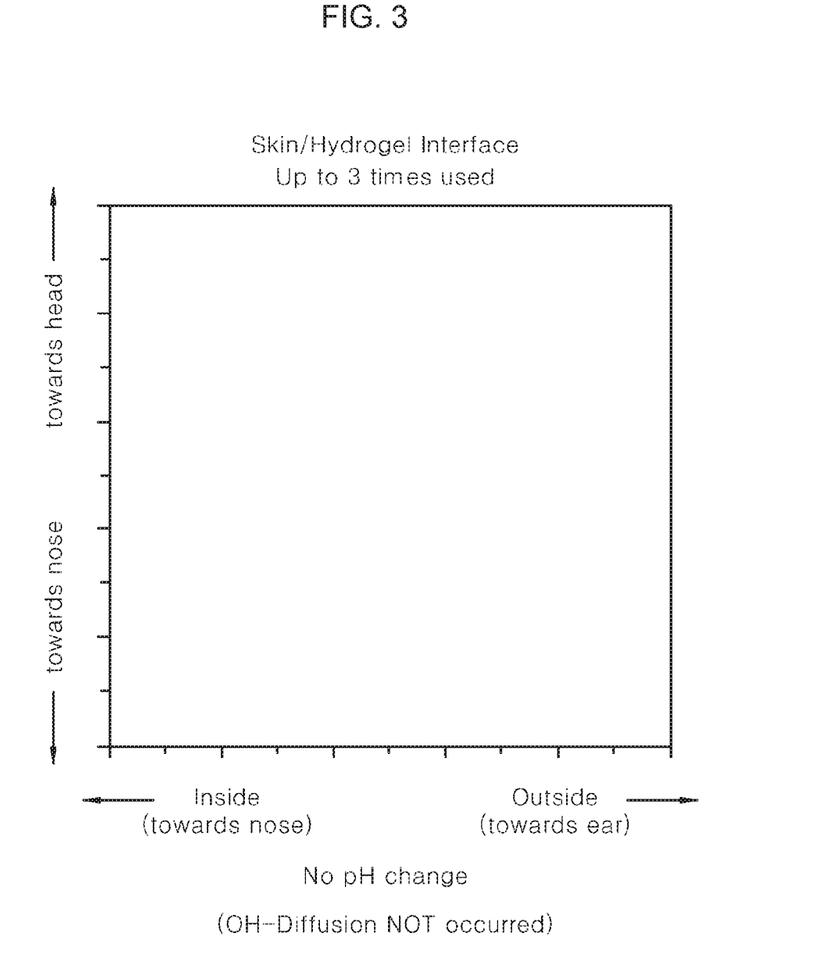
FIGS. 3 to 6 are views illustrating the results of neutralization experiments on a hydrogel patch of the stimulation electrode illustrated in FIG. 2.

FIG. 3 illustrates a pH state of the surface of the hydrogel patch 220 (i.e., the outer surface of the second hydrogel layer 224) that has been stimulated three times ("Up to 3 times used" in FIG. 6).

Referring to FIGS. 3 to 6, regardless of the number of use times of the hydrogel patch 220, it can be confirmed that there is little difference in pH state between the unused hydrogel patch 220 and the used hydrogel patch 220 obtained after lapse of a predetermined threshold period from the used time of the hydrogel patch 220. As a result, it can be recognized that the hydrogel patch 220 can be reused without damaging user skin tissues based on pH imbalance.

In other words, assuming that the hydrogel patch 220 is continuously stimulated for 60 minutes, OH— ions are diffused on the hydrogel patch, such that a pH value of the hydrogel patch is changed.

In accordance with one embodiment of the present disclosure, in order to utilize usability recovery characteristics of the hydrogel patch 220, the control unit 120 (see FIG. 1) may apply stimulation having a predetermined level capable of recovering the usability of the hydrogel patch 220 to the hydrogel patch 220. Thereafter, during a time period needed to recover the usability of the stimulated hydrogel patch, the control unit 120 is configured to control the transcranial direct current stimulation (tDCS) apparatus.

In other words, as can be seen from FIG. 1, the control unit 120 according to the embodiment of the present disclosure may receive information regarding the amount of power applied from the power-supply unit 112 to the stimulation electrodes 114 or information regarding the power supply time for the stimulation electrodes 114, and may establish an idle time corresponding to either the amount of power applied to the stimulation electrodes 114 or the power supply time for the stimulation electrodes 114 on the basis of the received information.

Therefore, the controller 120 may control the hydrogel patch of each of the stimulation electrodes 114 to receive power from the power-supply unit 112 within a maximum usage time (reference time) allowed for the hydrogel patch of the stimulation electrodes 114, and may establish a power-supply control time (prescribed time) corresponding to the amount of power applied to the stimulation electrodes 114 or the power supply time for the stimulation electrodes 114.

In more detail, if the amount of power applied from the power-supply unit 112 to the stimulation electrodes 114 or the power supply time for the stimulation electrodes 114 is longer than the reference time, the control unit 120 may mandatorily finish supply of the power applied to the stimulation electrodes 114. If power supply from the power-supply unit 112 is interrupted before reaching the reference time, the control unit 120 may calculate a prescribed time based on the amount of power or the power supply time, may establish the prescribed time, and may prevent the stimulation electrodes 114 from being powered on during the prescribed time. If the prescribed time is satisfied, i.e., if the time during which each of the stimulation electrodes 114 is not powered on is longer than the prescribed time, the transcranial direct current stimulation (tDCS) apparatus may remain in a standby mode in which the transcranial direct current stimulation (tDCS) apparatus can be reused.

In this case, it is obvious to those skilled in the art that the operation for allowing the control unit 120 to control power supply for the stimulation electrodes 114 can be implemented in various ways, for example, through a method for controlling the power-supply unit 112 or through a method for controlling a main power supply of the transcranial direct current stimulation (tDCS) apparatus 100.

For reference, although the embodiment of the present disclosure has disclosed only the transcranial direct current stimulation (tDCS) apparatus with reference to the attached drawings for convenience of description and better understanding of the present disclosure, the scope or spirit of the present disclosure is not limited to the transcranial direct current stimulation (tDCS) apparatus, and it is obvious to those skilled in the art that the technical idea of the present disclosure can also be applied to all kinds of DC stimulation apparatuses in which the aforementioned usability recovery characteristics of the hydrogel patch can be used. For example, assuming that the hydrogel patch is applied to a low-frequency therapeutic apparatus based on DC stimulation, the hydrogel patch may be reused through application of the same control method as in the embodiment of the present disclosure.

Each of the stimulation electrodes 114 of the transcranial direct current stimulation (tDCS) apparatus 110 according to the embodiment of the present disclosure may include a double-structured hydrogel patch 220 as shown in FIG. 2. That is, the stimulation electrode 114 may include a conductive body 210 such as a conductive carbon, a first hydrogel layer 222 which is in contact with the conductive body 210, and a second hydrogel layer 224 which is in close contact with the first hydrogel layer 222. The second hydrogel layer 224 may have a relatively higher impedance than the first hydrogel layer 222, and may be in direct contact with a living body such as the scarp.

A detailed configuration and functions of the stimulation electrodes 114 and the hydrogel patch 220 included in each of the stimulation electrodes 114 have been disclosed in Korean Patent Registration No. 10-1473433 (entitled "PATCH APPARATUS") filed by the same applicant as the present disclosure.

Figure 7:
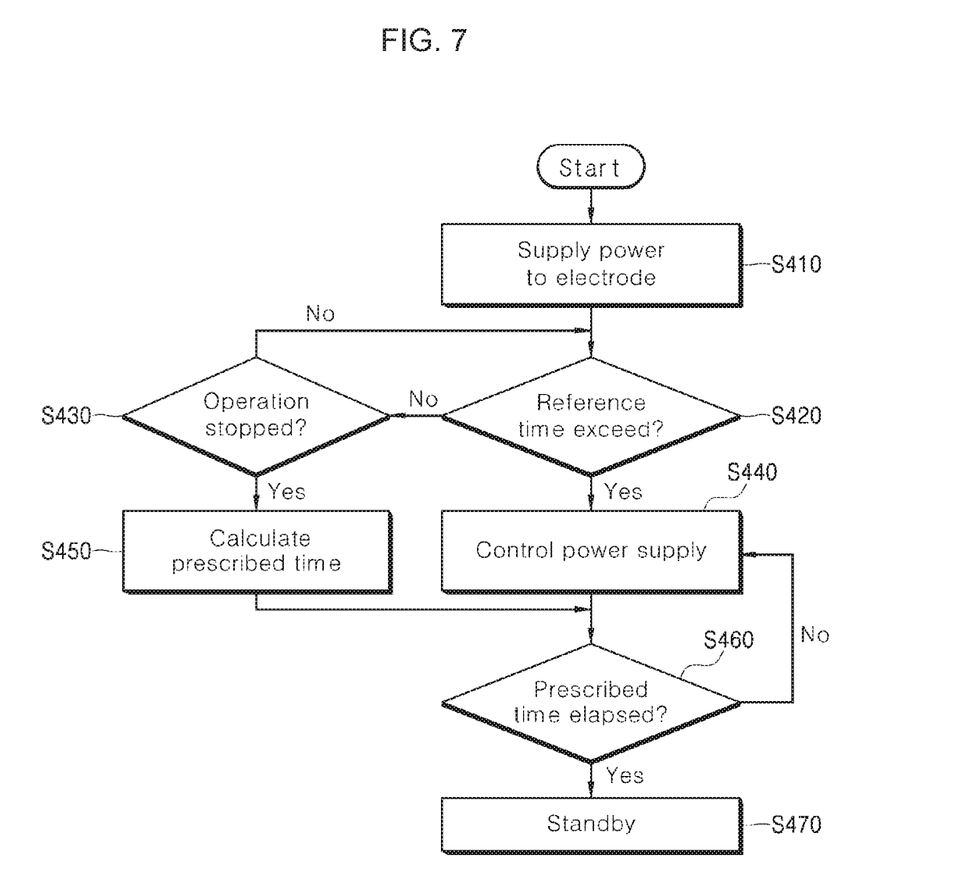
FIG. 7 is a flowchart illustrating a method for operating the transcranial direct current stimulation (tDCS) apparatus according to an embodiment of the present disclosure.

FIG. 7 is a flowchart illustrating a method for operating the transcranial direct current stimulation (tDCS) apparatus according to an embodiment of the present disclosure.

Referring to FIG. 7, the transcranial direct current stimulation apparatus (tDCS) apparatus according to the embodiment of the present disclosure may start operation when each of the stimulation electrodes is powered on (S410).

That is, the control unit 120 (see FIG. 1) may control power supply in a manner that each of the stimulation electrodes is powered on within the reference time (S420). If the power supply time for the stimulation electrodes is longer than the reference time (S420), the control unit 120 may control power supply for the stimulation electrodes (S440).

If the power supply for the stimulation electrodes is controlled as described above (S440), the control unit 120 may remain in the standby mode in which the transcranial direct current stimulation (tDCS) apparatus can be reused, after lapse of a prescribed time (S460).

In this case, if the transcranial direct current stimulation (tDCS) apparatus stops operation (S430) before reaching the reference time (S420), the control unit 120 may calculate the prescribed time using the amount of power supply or the power supply time (S450). After lapse of the calculated prescribed time (S460), the transcranial direct current stimulation (tDCS) apparatus may remain in the standby mode (S470) in which the transcranial direct current stimulation (tDCS) apparatus can be reused.

In this case, as previously stated above, the operation (S440) for controlling power supply for the stimulation electrodes may be achieved by controlling the power-supply unit (112 of FIG. 1) or by controlling functions of a main power supply of the transcranial direct current stimulation (tDCS) apparatus.

In addition, the above-mentioned control scheme according to the present disclosure can be applied not only to the transcranial direct current stimulation (tDCS) apparatus but also to various direct current stimulation devices, each of which uses the hydrogel patch.

Although the preferred embodiments of the present disclosure have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The above-mentioned control scheme according to the present disclosure can be applied not only to the transcranial direct current stimulation (tDCS) apparatus but also to various direct current stimulation devices, each of which uses the hydrogel patch.

The invention claimed is:

1. A transcranial direct current stimulation apparatus, comprising: a stimulation unit, a control unit, and an input/output (I/O) unit,
    the stimulation unit including
        a power-supply unit configured to supply power for electrical stimulation corresponding to a control signal received from the control unit; and
        a plurality of stimulation electrodes, each of which has a hydrogel patch, configured to provide electrical stimulation to a living body upon receiving the power from the power-supply unit,
    wherein
    the control unit is configured to control an ON/OFF function of the power-supply unit in a manner that the power-supply unit is turned on or off according to an amount of power applied to each of the stimulation electrodes and a time period during which the power is supplied or not supplied,
    the control unit is configured to control the ON function of the power-supply unit during a prescribed time in a manner that the power-supply unit is turned on according to the amount of power applied to each of the stimulation electrodes or a continuous power supply time for each stimulation electrode, the control unit is configured to recover usability of each of the hydrogel patches used at least one time for the electric stimulation by turning on the power-supply unit to apply power to each of the stimulation electrodes in response to a determination that a time during which each of the stimulation electrodes is not powered on is longer than the prescribed time, and the control unit is configured to, in response to determining that the power supply from the power-supply unit is stopped before reaching a maximum usage time for each of the hydrogel patches, calculate the prescribed time based on the amount of power applied to each of the stimulation electrodes or the power supply time for each stimulation electrode.

2. The transcranial direct current stimulation apparatus of claim 1, wherein:

the control unit is configured to turn off the power-supply unit when the amount of power applied to each of the stimulation electrodes or the power supply time for each stimulation electrode is greater than a reference value.

3. The transcranial direct current stimulation apparatus of claim 2, wherein the control unit is configured to calculate and establish, in real time, a reference power-supply value capable of being applied to each stimulation electrode in a manner that the reference power-supply value corresponds to a time period during which power is not supplied to each of the stimulation electrodes.

4. The transcranial direct current stimulation apparatus of claim 1, wherein the prescribed time is established by real-time calculation of the control unit in a manner that the prescribed time corresponds to the amount of power applied to each of the stimulation electrodes or the power supply time for each stimulation electrode.

5. The transcranial direct current stimulation apparatus of claim 4, wherein each of the stimulation electrodes includes:
 a conductive body; and
 the hydrogel patch including
  a first hydrogel layer which is in contact with the conductive body; and
  a second hydrogel layer which has a relatively higher impedance than the first hydrogel layer, and is in contact with the living body.

6. The transcranial direct current stimulation apparatus of claim 2, wherein the prescribed time is established by real-time calculation of the control unit in a manner that the prescribed time corresponds to the amount of power applied to each of the stimulation electrodes or the power supply time for each stimulation electrode.

7. The transcranial direct current stimulation apparatus of claim 3, wherein the prescribed time is established by real-time calculation of the control unit in a manner that the prescribed time corresponds to the amount of power applied to each of the stimulation electrodes or the power supply time for each stimulation electrode.

8. The transcranial direct current stimulation apparatus of claim 1, wherein the hydrogel patch is reusable when the power-supply unit is turned on to apply power to each of the stimulation electrodes in response to the determination that the time during which each of the stimulation electrodes is not powered on is longer than the prescribed time.

* * * * *